United States Patent
Clement

(10) Patent No.: US 8,373,025 B2
(45) Date of Patent: Feb. 12, 2013

(54) HERBICIDE RESISTANT SORGHUM

(75) Inventor: Edward L. Clement, Victoria, TX (US)

(73) Assignee: Chromatin Germplasm, LLC

( * ) Notice: Subject to any disclaimer, the term of this patent is extended or adjusted under 35 U.S.C. 154(b) by 278 days.

(21) Appl. No.: 12/700,276

(22) Filed: Feb. 4, 2010

(65) Prior Publication Data

US 2010/0205686 A1 Aug. 12, 2010

Related U.S. Application Data

(60) Provisional application No. 61/150,963, filed on Feb. 9, 2009.

(51) Int. Cl.
*A01H 1/00* (2006.01)
*A01H 4/00* (2006.01)
*A01H 5/00* (2006.01)
*A01H 5/10* (2006.01)

(52) U.S. Cl. ........ 800/300; 435/410; 800/260; 800/298; 800/320

(58) Field of Classification Search .......... None
See application file for complete search history.

(56) References Cited

U.S. PATENT DOCUMENTS 5,888,818 A 3/1999 Cronin et al.

FOREIGN PATENT DOCUMENTS

WO WO-93/24637 12/1993

OTHER PUBLICATIONS

Anthony et al 1999, Trends in Plant Science Reviews 4(3): 112-116.*
Dweikat 2005 Molecular Breeding 16: 93-101.*
U.S. Appl. No. 11/951,629, filed Sep. 4, 2008, Tuinstra, Mitchell R., et al.
U.S. Appl. No. 12/066,803, filed Oct. 16, 2008, Panayi, Aristos, et al.
Heap, 1997. The Occurrence of Herbicide-Resistant Weeds Worldwide. Pesticide Science, vol. 51, No. 3:235-243.
Anthony, et al. 1999. Dinitroaniline herbicide resistance and the microtubule cytoskeleton. Trends in Plant Science, vol. 4, No. 3:112-116.
Anthony, et al., 1999. Dinitroaniline herbicide-resistant transgenic tobacco plants generated by co-overexpression of a mutant $\alpha$-tubulin and a $\beta$-tubulin. Nature Biotechnology, vol. 17, No. 7:712-716.
Anthony, et al., 1998. Herbicide resistance caused by spontaneous mutation of the cytoskeletal protein tubulin. Nature, Nature Publishing Group, vol. 393, No. 6682:260-263.
Grichar, et al., 2005. Weed Control and Grain Sorghum (*Sorghum bicolor*) Response to Postemergence Applications of Atrazine, Pendimethalin, and Trifluralin, Weed Technology, vol. 19:999-1003.
Ramakrishna, 2003. Integrated weed management improves grain sorghum growth and yield on Vertisols. Tropical Agriculture, vol. 80, No. 1:48-53.
Poehlman, et al., 1959. Breeding Sorghum. Breeding Field Crops, University of Missouri, Ch. 14:279-301.

* cited by examiner

*Primary Examiner* — David H Kruse
(74) *Attorney, Agent, or Firm* — Marshall, Gerstein & Borun LLP

(57) ABSTRACT

Sorghum genotypes that exhibit resistance to dinitroanaline herbicides are disclosed. The invention relates to the seeds of sorghum genotypes with resistance to dinitroanaline herbicides, to the plants of sorghum genotypes with resistance to dinitroanaline herbicides, to plant parts of sorghum genotypes with resistance to dinitroanaline herbicides and to methods for producing a sorghum plant produced by crossing of one or more sorghum genotypes with resistance to dinitroanaline herbicides with itself or with another sorghum plant.

13 Claims, No Drawings

HERBICIDE RESISTANT SORGHUM

CROSS-REFERENCE TO RELATED APPLICATIONS

This application is a non-provisional application of U.S. Provisional Patent Application No. 61/150,963 filed on Feb. 9, 2009, which is herein incorporated by reference in its entirety.

BACKGROUND

The present invention relates to sorghum plants having a resistance or tolerance to dinitroanaline herbicides. All publications cited in this application are herein incorporated by reference.

Sorghum is the second most important cereal-feed grain grown in the United States. Production is economically critical to farms operating in marginal rainfall areas because of sorghum's ability to tolerate drought and heat. Both the livestock and bio-energy industries utilize sorghum as an energy substrate thereby making it a versatile crop.

Worldwide, sorghum is the fifth leading cereal grain. As it is tolerant to both drought and heat, it is easily the most widely grown food grain in the semiarid regions of sub-Sahelian Africa and in the dry central peninsular region of India. As such, sorghum is used in human consumption in most of the driest regions of the world thereby making it a critically important food crop in these locations.

The goal of plant breeding is to combine in a single variety or hybrid various desirable traits of the parental lines. For field crops, these traits may include resistance to diseases and insects, tolerance to heat, drought and salt, reducing the time to crop maturity, greater yield and yield stability and better agronomic quality. With mechanical harvesting of many crops, uniformity of plant characteristics such as germination and stand establishment, growth rate, maturity, plant height and fruit size, is important.

Field crops are bred through techniques that take advantage of the plant's method of pollination. A plant is self-pollinating if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous plants from differing backgrounds or two homozygous lines produce a uniform population of hybrid plants that may be heterozygous for many gene loci. A cross of two plants each heterozygous at a number of gene loci will produce a population of hybrid plants that differ genetically and will not be uniform.

Sorghum plants are bred in most cases by self-pollination techniques. With the incorporation of male sterility (either genetic or cytoplasmic) cross-pollination breeding techniques can also be utilized. Sorghum has a perfect flower with both male and female parts in the same flower located in the panicle. The flowers are usually in pairs on the panicle branches. Natural pollination occurs in sorghum when anthers (male part of flowers) open and pollen falls onto receptive stigma (female part of flowers). Because of the close proximity of male (anthers) and female (stigma) in the panicle, self-pollination is very high (average 94%). Cross-pollination may occur when wind or convection currents move pollen from the anthers of one plant to receptive stigma on another plant. Cross-pollination is greatly enhanced with incorporation of male sterility, which renders the anthers (male part of flowers) nonviable without affecting the stigmas (female part of flowers). Successful pollination in the case of male sterile flowers requires cross-pollination.

The development of sorghum hybrids requires the development of homozygous inbred lines, the crossing of these lines, and the evaluation of the crosses. Pedigree breeding methods, and to a lesser extent population breeding methods, are used to develop inbred lines from breeding populations. Breeding programs combine desirable traits from two or more inbred lines into breeding pools from which new inbred lines are developed by selfing and selection of desired phenotypes. The new inbreds are crossed with other inbred lines and the hybrids from these crosses are evaluated to determine which have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically, in the pedigree method of breeding five or more generations of selfing and selection is practiced. $F_1$ to $F_2$; $F_2$ to $F_3$; $F_3$ to $F_4$, $F_4$ to $F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate genes(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

A hybrid sorghum variety is the cross of two inbred lines, each of which may have one or more desirable characteristics lacked by the other or which complement the other. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

The development of a hybrid sorghum variety involves five steps: (1) the formation of "restorer" and "non-restorer" germplasm pools; (2) the selection of superior plants from various "restorer" and "non-restorer" germplasm pools; (3) the selfing of the superior plants for several generations to produce a series of inbred lines, which although different from each other, each breed true and are highly uniform; (4) the conversion of inbred lines classified as non-restorers to cytoplasmic male sterile (CMS) forms, and (5) crossing the selected cytoplasmic male sterile (CMS) inbred lines with selected fertile inbred lines (restorer lines) to produce the hybrid progeny ($F_1$).

Because sorghum is normally a self-pollinated plant and because both male and female flowers are in the same panicle, large numbers of hybrid seed can only be produced by using cytoplasmic male sterile (CMS) inbreds. Flowers of the CMS inbred are fertilized with pollen from a male fertile inbred carrying genes which restore male fertility in the hybrid ($F_1$) plants. An important consequence of the homozygosity and homogeneity of the inbred lines is that the hybrid between any two inbreds will always be the same, absent mutation. Once the inbreds that give the best hybrid have been identified, the hybrid seed can be reproduced indefinitely as long as the homogeneity of the inbred parent is maintained.

A single cross hybrid is produced when two inbred lines are crossed to produce the $F_1$ progeny. Much of the hybrid vigor exhibited by $F_1$ hybrids is lost in the next generation ($F_2$). Consequently, seed from hybrid varieties is not used for planting stock.

Hybrid grain sorghum can be produced using wind to move the pollen. Alternating strips of the cytoplasmic male sterile inbred (female) and the male fertile inbred (male) are planted in the same field. Wind moves the pollen shed by the male inbred to receptive stigma on the female. Providing that there is sufficient isolation from sources of foreign sorghum pollen, the stigma of the male sterile inbred (female) will be fertilized only with pollen from the male fertile inbred (male). The resulting seed, borne on the male sterile (female) plants is therefore hybrid and will form hybrid plants that have full fertility restored.

Grain sorghum is an important and valuable food and feed grain crop. In addition, its vegetative parts are used for forage, syrup and shelter. Thus, a continuing goal of plant breeders is to develop stable high yielding sorghum hybrids that are agronomically sound. The reasons for this goal are to maximize the amount of grain produced on the land used and to supply food for both animals and humans.

SUMMARY OF THE INVENTION

One aspect of the present invention provides for sorghum plants and methods for producing sorghum plants that are resistant or tolerant to herbicides. In another aspect, the present invention provides for sorghum plants, plant tissues and plant seeds that are resistant or tolerant to dinitroanaline herbicides.

A further aspect of the present invention is to produce one or more sorghum plants whose DNA comprises a mutation called SP6493 that renders the plant resistant or tolerant to dinitroanaline herbicides. Moreover, in further embodiments, the invention relates to the offspring (e.g., $F_1$, $F_2$, $F_3$, $F_4$, $F_5$, $F_6$, $F_7$, $F_8$ and $F_9$ or more) of a cross of the plant wherein the DNA of the offspring has the same mutation as the parent plant for resistance or tolerance to dinitroanaline herbicides. Therefore, embodiments of the present invention provide for sorghum plants, inbreds, restorers and hybrids whose DNA contains a mutation SP6493, such that the phenotype of the plants is dinitroanaline herbicide resistant or tolerant.

It is another aspect of the present invention to provide a sorghum plant wherein the sorghum plant confers a level of resistance to one or more dinitroanalines herbicides at variable levels of one or more herbicides that would normally inhibit the growth of a sorghum plant.

Another aspect of the invention is to provide methods for producing additional sorghum plants derived from a sorghum plant having the SP6493 allele. Sorghum lines derived by the use of those methods are also part of the invention.

Another aspect of the invention also relates to methods for producing a sorghum plant containing in its genetic material one or more transgenes and to the transgenic sorghum plant produced by that method.

Another aspect of the invention further provides methods for developing sorghum plants in a sorghum plant breeding program using plant breeding techniques including recurrent selection, backcrossing, pedigree breeding, restriction fragment length polymorphism enhanced selection, genetic marker enhanced selection and transformation.

Another aspect of the invention relates to sorghum cultivars or breeding cultivars and plant parts derived from a sorghum plant with resistance to dinitroanaline herbicides, to methods for producing other sorghum cultivars, lines or plant parts derived from sorghum plants with resistance to dinitroanaline herbicides.

Another aspect of the invention relates to hybrid sorghum seeds, plants and plant parts produced by crossing a sorghum plant with resistance to dinitroanaline herbicides with another sorghum cultivar.

Another aspect of the invention further provides a herbicide resistant sorghum plant, wherein the plant has a mean percent increased resistance to dinitroanaline herbicides which is 10.0% or greater than the resistance of susceptible sorghum lines. The mean percent increase in resistance to dinitroanaline herbicides is between 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, 15.0%, 15.1%, 15.2%, 15.3%, 23.0%, 31.4%, 37.2%, 42.1%, 49.7%, 53.8%, 68.2%, 74.6%, 86.7%, 93.3%, 106.0%, 115.4%, 128.8%, 136.4%, 145.1%, 162.1%, 178.9%, 196.6%, 212.5%, 250.4%, 310.6%, 364.4%, 421.1%, 586.0%, 678.7% and 850.9% or higher and including all integers and fractions thereof.

In addition to the exemplary aspects and embodiments described above, further aspects and embodiments will become apparent by study of the following descriptions.

DEFINITIONS

Allele. As used herein "allele" refers to any of one or more alternative forms of a gene, all of which alleles relate to one trait or characteristic. In a diploid cell or organism, the two alleles of a given gene occupy corresponding loci on a pair of homologous chromosomes.

Backcrossing. As used herein "backcrossing" refers to a process in which a breeder repeatedly crosses hybrid progeny back to one of the parents, for example, a first generation hybrid $F_1$ with one of the parental genotypes of the $F_1$ hybrid.

Derivative. As used herein "derivative" refers to an herbicide resistant plant includes both the progeny of that herbicide resistant plant, as well as any mutant, recombinant, or genetically engineered derivative of that plant, whether of the same species or a different species, where the herbicide resistant characteristic(s) of the original herbicide resistant plant has been transferred to the derivative plant.

Dinitroanalines. As used herein "dinitroanaline" refers to a class of broad-spectrum dinitroanaline herbicides that inhibit new plant growth in plants and are used to control many grasses and broadleaf weeds. Dinitroanalines are incorporated in soil to control weeds in many important crops such as sorghum, soybean, cotton, tobacco, tomatoes, cereals, canola, pulses and legume crops. An example may include the commercial herbicide Treflan® or Prowl® $H_2O$.

Dinitroanilines are of general formula shown below:

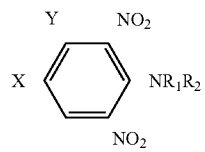

wherein X is selected from lower alkyl, halogenated lower alkyl, lower alkyl sulfonyl and amino sulfonyl;
Y is hydrogen or lower alkyl
R.sub.1 is hydrogen or lower alkyl: and
R.sub.2 is lower alkyl, lower alkenyl or halogenated lower alkyl.
The lower alkyl/alkenyl fragments are typically C.sub.1 to C.sub.4 alkyl/C.sub.2 to C.sub.4 alkenyl.

Essentially all the physiological and morphological characteristics. As used herein refers to a plant having essentially all the physiological and morphological characteristics of the cultivar, except for the characteristics derived from the converted gene.

Germplasm. As used herein "germplasm" refers to any genetic material of a plant that contains functional units of heredity, including but not limited to DNA.

Hybrid. As used herein "hybrid" refers to $F_1$ seed or plant produced from crossing two or more parental lines or populations.

Marker and DNA marker and molecular marker. As used herein "marker and DNA marker and molecular marker" refers to a physiological or morphological trait that may be determined as a marker for its own selection or for selection of other traits closely linked to that marker. For example, such a marker could be a gene or trait that associates with herbicide tolerance including, but not limited to, simple sequence repeat (SSR), single nucleotide polymorphism (SNP), genetic insertions and/or deletions and the like.

Mutation. As used herein "mutation" refers to a permanent change in the DNA sequence of an allele such as the SP6493 mutation of the present invention.

Percent increased resistance. As used herein, "percent increased resistance" means the percent difference in the average amount of emergence from the soil of sorghum plant lines that are resistant to dinitroanaline herbicides versus the average amount of emergence from the soil of sorghum plant lines that are susceptible to dinitroanaline herbicides at a given time or date. For example, if an average of twenty plants of one sorghum genotype emerge from the soil versus an average of ten plants of a second sorghum genotype that emerge from the soil in the same test and location, then the percent increased resistance for the first genotype will equal 100% versus the second genotype. The mean percent increase in resistance to dinitroanaline herbicides is 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, 15.0%, 15.1%, 15.2%, 15.3%, 23.0%, 31.4%, 37.2%, 42.1%, 49.7%, 53.8%, 68.2%, 74.6%, 86.7%, 93.3%, 106.0%, 115.4%, 128.8%, 136.4%, 145.1%, 162.1%, 178.9%, 196.6%, 212.5%, 250.4%, 310.6%, 364.4%, 421.1%, 586.0%, 678.7% and 850.9% or higher and including all integers and fractions thereof.

Plant tissue. As used herein "plant tissue" refers to differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture.

Plant part. As used herein "plant part" refers to plant material selected from the group consisting of protoplasm, leaf, pollen, embryo, cotyledon, hypocotyl, meristematic cell, root, root tip, pistil, anther, flower, ovule, shoot, stem, seed and petiole.

Progeny. As used herein "progeny" refers to generations of a plant, wherein the ancestry of the generation can be traced back to the same source plant. For example progeny includes an $F_1$ sorghum plant produced from the cross of two sorghum plants where at least one plant includes hybrid sorghum and progeny further includes but is not limited to subsequent $F_2$, $F_3$, $F_4$, $F_5$, $F_6$, $F_7$, $F_8$, $F_9$ and $F_{10}$ generational crosses with the recurrent parental line.

Quantitative Trait Loci (QTL). As used herein "quantitative trait loci" refers to genetic loci that control to some degree numerically representable traits that are usually continuously distributed.

Resistant. As used herein "resistant" means a plant resistant or able to tolerate herbicide concentrations or levels (e.g., herbicides such as dinitroanaline herbicides) which are harmful to other plants of the same species.

Regeneration. As used herein, "regeneration" means the development of a plant from tissue culture.

Single Gene Converted (Conversion). As used herein "single gene converted" refers to plants which are developed by a plant breeding technique called backcrossing wherein essentially all of the desired morphological and physiological characteristics of a variety are recovered in addition to the single gene transferred into the variety via the backcrossing technique or via genetic engineering.

Sorghum. As used herein "Sorghum" includes all species within the genus *Sorghum* including but not limited to *Sorghum bicolor, Sorghum halepense, Sorghum almum, Sorghum sudanense*, and *Sorghum propinquum*.

SP6493. As used herein "SP6493" refers to one or more mutant alleles in seed and plants that confer resistance or tolerance to dinitroanaline herbicides.

Susceptible sorghum. As used herein "susceptible sorghum" refers to sorghum plants that do not have the SP6493 mutation.

Tolerance. As used herein "tolerance" means a plant able to tolerate herbicide concentrations or levels (e.g., herbicides such as dinitroanaline herbicides) which are harmful to other plants of the same species.

Trait or Phenotype. As used herein, "trait" or "phenotype" means an observable and/or measurable characteristic of an organism. For example, the present invention describes plants that are dinitroanaline herbicide resistant.

Wild-type. As used herein, "wild-type" means a functional gene common throughout a plant population. A functional wild-type gene is that which is most frequently observed in a population and is thus arbitrarily designated the "normal" or "wild-type" form of the gene.

DETAILED DESCRIPTION OF THE INVENTION

One aspect of the present invention provides for one or more sorghum plants whose DNA comprises a mutation named SP6493 that renders the plant resistant or tolerant to dinitroanalines herbicides. Moreover, in further embodiments, the invention relates to the offspring (e.g., $F_1$, $F_2$, $F_3$, $F_4$, $F_5$, $F_6$, $F_7$, $F_8$, $F_9$ or more) of a cross of said plant wherein the DNA of said offspring has the same mutation as the parent plant rendering the plant resistant or tolerant to dinitroanalines. Therefore, embodiments of the present invention provide for sorghum hybrids whose DNA contains a mutation which results in plants that are dinitroanalines herbicide resistant.

The present invention further encompasses sorghum plants having a percent increased resistance to dinitroanaline herbicides when compared to sorghum plants susceptible to dinitroanaline herbicides where the mean percent increase in resistance to dinitroanaline herbicides is 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, 15.0%, 15.1%, 15.2%, 15.3%, 23.0%, 31.4%, 37.2%, 42.1%, 49.7%, 53.8%, 68.2%, 74.6%, 86.7%, 93.3%, 106.0%, 115.4%, 128.8%, 136.4%, 145.1%, 162.1%, 178.9%, 196.6%, 212.5%, 250.4%, 310.6%, 364.4%, 421.1%, 586.0%, 678.7% and 850.9% or higher and including all integers and fractions thereof.

Cultivated sorghum is susceptible to many dinitroanaline herbicides that target monocot, or grassy species. However, as described herein a sorghum genotype and mutation of the present invention exhibits resistance to dinitroanaline herbicides.

The development of herbicide resistance in plants offers significant production and economic advantages; as such the use of herbicides for controlling weeds in crops has become almost a universal practice. However, application of such herbicides can also result in death or reduced growth of the desired crop plant, making the timing and method of herbicide application critical or in some cases unfeasible.

Of particular interest to farmers is the use of herbicides with greater potency, broad weed spectrum effectiveness and rapid soil degradation. Plants, plant tissues and seeds with resistance to these compounds provide an attractive solution by allowing the herbicides to be used to control weed growth, with small risk of damage to the crop. One such class of broad-spectrum herbicides is those that inhibit new plant growth called dinitroanalines. Dinitroanaline (more specifically 2,6-dinitroanalines such as the commercial product TREFLAN® or Prowl® $H_2O$) are a group of herbicides used to control many grasses and broadleaf weeds. The dinitroanalines are most commonly used as pre-emergent herbicides and are incorporated in soil to control weeds in many important crops such as sorghum, soybean, cotton, tobacco, tomatoes, cereals, canola, pulses and legume crops.

Dinitroanalines may be formulated as concentrates for dilution with water at the time of use, for example in a spray tank. In order to minimize solvent use and transport cost it is desirable to use a concentrated solution of dinitroanalines which can be diluted prior to use. Concentrated solutions of dinitroanalines are generally not physically stable as they tend to crystallize, particularly at low temperatures. Commercial concentrate formulations of dinitroanalines such as trifluralin and pendimethalin generally have concentrations of about 40-50% and 30-45% respectively.

Attempts have been made to stabilize dinitroanalines using different solvents but often the solvents required such as toluene and xylene are highly flammable and would require special facilities to be used to meet safety requirements for highly flammable solvents. Accordingly some of the proposals for concentrates add significantly to the cost and risks associated with transport and storage.

For many herbicides it is the practice to incorporate fertilizer in the diluted compositions prepared from herbicidal concentrates in a spray tank prior to application. As compositions containing a liquid nitrogen fertilizer and dinitroanalines are often not homogeneous mixtures, they typically require constant and vigorous agitation in order to ensure adequate mixing of the fertilizer and herbicide prior to use.

Example 1

Development of SP6493

Two hundred and sixty four proprietary inbred lines and hybrid lines were planted in Victoria, Tex. in July 2006 in soil that was treated with the herbicide Treflan®. Only five plants in one plot emerged from the soil that was treated with the herbicide, all other plants were killed by the Treflan® (about 250-300 seeds were planted in each plot). These five plants were identified to contain the SP6493 mutation for increased resistance to dinitroanaline herbicides, were grown to maturity and given codes Treflan-Res-1, Treflan-Res-2, Treflan-Res-3, Treflan-Res-4 and Treflan-Res-5. Pollen from some of these plants was also crossed onto susceptible female sorghum plants not planted in soil treated with the herbicide Treflan® to produce hybrids that were evaluated in 2007 and 2008 which indicated the type of genetic resistance involved in dinitroanaline herbicide resistance.

A. Examples of Sorghum Crosses Made with Dinitroanaline Resistance

In June, 2008, eight crosses were made between the proprietary mutant SP6493 Treflan-Res selections containing the mutation for increased resistance to dinitroanaline herbicides and crossed with eight susceptible proprietary sorghum lines. The F1 seed from these crosses were planted in late July 2008 in Victoria, Tex.

Example 2

Inbred Cross of Sorghum M42 and Treflan-RES-1

Sorghum M42 was crossed with TREFLAN-RES-1 in June 2008. F2 populations derived from crosses with these parents were evaluated to determine tolerance to dinitroanalines. Treflan® herbicide was applied at the rate of one quart per acre mixed in 20 gallons of water per acre. Treflan® and water were mixed in a self-propelled ground spray rig and sprayed in a broadcast pattern (the entire soil area was sprayed). After spraying, the Treflan® was incorporated into the soil with a tandem double disc prior to planting sorghum seed.

Example 3

Inbred Cross of Sorghum R207 and Treflan-RES-1

Sorghum R207 was crossed with TREFLAN-RES-1 in June 2008. F2 populations derived from crosses with these parents were evaluated to determine tolerance to dinitroanalines. Treflan® herbicide was applied at the rate of one quart per acre mixed in 20 gallons of water per acre. Treflan® and water were mixed in a self-propelled ground spray rig and sprayed in a broadcast pattern (the entire soil area was sprayed). After spraying, the Treflan® was incorporated into the soil with a tandem double disc prior to planting sorghum seed.

Example 4

Inbred Cross of Sorghum R441 and Treflan-RES-1

Sorghum R441 was crossed with TREFLAN-RES-1 in June 2008. F2 populations derived from crosses with these parents were evaluated to determine tolerance to dinitroanalines. Treflan® herbicide was applied at the rate of one quart per acre mixed in 20 gallons of water per acre. Treflan® and water were mixed in a self-propelled ground spray rig and sprayed in a broadcast pattern (the entire soil area was sprayed). After spraying, the Treflan® was incorporated into the soil with a tandem double disc prior to planting sorghum seed.

Example 5

Inbred Cross of Sorghum R436 and Treflan-RES-1

Sorghum inbred R436 was crossed with TREFLAN-RES-1 in June 2008. F2 populations derived from crosses with these parents were evaluated to determine tolerance to dinitroanalines. Treflan® herbicide was applied at the rate of one quart per acre mixed in 20 gallons of water per acre. Treflan® and water were mixed in a self-propelled ground spray rig and sprayed in a broadcast pattern (the entire soil area was sprayed). After spraying, the Treflan® was incorporated into the soil with a tandem double disc prior to planting sorghum seed.

Example 6

Inbred Cross of Sorghum R440 and Treflan-RES-1

Sorghum R440 was crossed with TREFLAN-RES-1 in June 2008. F2 populations derived from crosses with these parents were evaluated to determine tolerance to dinitroanalines. Treflan® herbicide was applied at the rate of one quart per acre mixed in 20 gallons of water per acre. Treflan® and water were mixed in a self-propelled ground spray rig and sprayed in a broadcast pattern (the entire soil area was sprayed). After spraying, the Treflan® was incorporated into the soil with a tandem double disc prior to planting sorghum seed.

Example 7

Inbred Cross of Sorghum R442 and Treflan-RES-1

Sorghum R442 was crossed with TREFLAN-RES-1 in June 2008. F2 populations derived from crosses with these parents were evaluated to determine tolerance to dinitroanalines. Treflan® herbicide was applied at the rate of one quart per acre mixed in 20 gallons of water per acre. Treflan® and water were mixed in a self-propelled ground spray rig and sprayed in a broadcast pattern (the entire soil area was sprayed). After spraying, the Treflan® was incorporated into the soil with a tandem double disc prior to planting sorghum seed.

Example 8

Inbred Cross of Sorghum RF 124 and Treflan-RES-2

Sorghum RF 124 was crossed with TREFLAN-RES-2 in June 2008. F2 populations derived from crosses with these parents were evaluated to determine tolerance to dinitroanalines. Treflan® herbicide was applied at the rate of one quart per acre mixed in 20 gallons of water per acre. Treflan® and water were mixed in a self-propelled ground spray rig and sprayed in a broadcast pattern (the entire soil area was sprayed). After spraying, the Treflan® was incorporated into the soil with a tandem double disc prior to planting sorghum seed.

Example 9

Inbred Cross of Sorghum RM 4 and Treflan-RES-2

Sorghum RM 4 was crossed with TREFLAN-RES-2 in June 2008. F2 populations derived from crosses with these parents were evaluated to determine tolerance to dinitroanalines. Treflan® herbicide was applied at the rate of one quart per acre mixed in 20 gallons of water per acre. Treflan® and water were mixed in a self-propelled ground spray rig and sprayed in a broadcast pattern (the entire soil area was sprayed). After spraying, the Treflan® was incorporated into the soil with a tandem double disc prior to planting sorghum seed.

B. Examples of Hybrid Sorghum Having Resistance to Dinitroanalines.

In June, 2008, four hybrids were made between the Treflan-Res inbred lines containing the SP6493 mutation for increased resistance to dinitroanaline herbicides and crossed with two susceptible proprietary inbred steriles. The seed from these crosses were planted in late July in 2008 in Victoria, Tex.

Example 10

Hybrid Cross of Sorghum Inbred A821 and Treflan-RES-1

Sorghum inbred A821 was crossed with TREFLAN-RES-1 in June 2008. Hybrid seed derived from crosses with these parents were evaluated to determine tolerance to dinitroanalines. Treflan® herbicide was applied at the rate of one quart per acre mixed in 20 gallons of water per acre. Treflan® and water were mixed in a self-propelled ground spray rig and sprayed in a broadcast pattern (the entire soil area was sprayed). After spraying, the Treflan® was incorporated into the soil with a tandem double disc prior to planting sorghum seed.

Example 11

Hybrid Cross of Sorghum Inbred A821 and Treflan-RES-2

Sorghum inbred A821 was crossed with TREFLAN-RES-2 in June 2008. Hybrid seed derived from crosses with these parents were evaluated to determine tolerance to dinitroanalines. Treflan® herbicide was applied at the rate of one quart per acre mixed in 20 gallons of water per acre. Treflan® and water were mixed in a self-propelled ground spray rig and sprayed in a broadcast pattern (the entire soil area was sprayed). After spraying, the Treflan® was incorporated into the soil with a tandem double disc prior to planting sorghum seed.

Example 12

Hybrid Cross of Sorghum Inbred A752 and Treflan-RES-1

Sorghum inbred A752 was crossed with TREFLAN-RES-1 in June 2008. Hybrid seed derived from crosses with these parents were evaluated to determine tolerance to dinitroanalines. Treflan® herbicide was applied at the rate of one quart per acre mixed in 20 gallons of water per acre. Treflan® and water were mixed in a self-propelled ground spray rig and sprayed in a broadcast pattern (the entire soil area was sprayed). After spraying, the Treflan® was incorporated into the soil with a tandem double disc prior to planting sorghum seed.

Example 13

Hybrid Cross of Sorghum Inbred A752 and Treflan-RES-2

Sorghum inbred A752 was crossed with TREFLAN-RES-2 in June 2008. Hybrid seed derived from crosses with these parents were evaluated to determine tolerance to dinitroanalines. Treflan® herbicide was applied at the rate of one quart per acre mixed in 20 gallons of water per acre. Treflan® and water were mixed in a self-propelled ground spray rig and sprayed in a broadcast pattern (the entire soil area was sprayed). After spraying, the Treflan® was incorporated into the soil with a tandem double disc prior to planting sorghum seed.

C. Examples Field Test of Sorghum Resistance

The inbreds Treflan-Res-1 and Treflan-Res-2 were recoded as SP6493-1 and SP6493-2 respectively and bulked as SP6493.

Example 14

2009 Field Trials

On Nov. 2, 2009, a test was established in Victoria, Tex. Six sorghum lines susceptible to Prowl® $H_2O$ and one sorghum line containing the SP6493 mutation with resistance to Prowl® $H_2O$ were planted to determine the effects of Prowl® $H_2O$ on each line. The inbred sorghum line SP6493 with resistance to Prowl® $H_2O$ was compared to herbicide susceptible inbred sorghum lines R207, R159, T13, Early Sumac, R267 and R422. The hybrid sorghum (A752×SP6493) containing the SP6493 mutation with resistance to Prowl® $H_2O$ was also compared to the hybrid sorghum (A752×R427) that did not have resistance to Prowl® $H_2O$. Both the resistant hybrid (A752×SP6493) and the susceptible hybrid (A752× R427) have the same inbred female parent line A752 but the resistant hybrid sorghum line had the male parent SP6493 with resistance to Prowl® $H_2O$ while the susceptible hybrid line did not have this male parent.

Plastic flats measuring 11"×14"×3" were filled with a potting soil mixture. Four rows about one inch deep were made on each side of the flat. Twenty-five seeds were space planted per row for a total of 100 seeds of each line planted per flat. After planting, the seeds were covered with the potting soil mixture to a depth of approximately one inch. Each flat contained SP6493 as the inbred line with resistance to Prowl® $H_2O$. In addition, one herbicide susceptible inbred line was planted in each flat to compare with inbred line SP6493, providing a total of six comparisons. Both the hybrid sorghum (A752×SP6493) with resistance to Prowl® $H_2O$ and the hybrid sorghum (A752×R427) susceptible to Prowl® $H_2O$ were planted in one flat with 100 seed planted of each hybrid.

Seeds were planted on Nov. 2, 2009. After planting, the flats were watered with a mixture containing Prowl® $H_2O$. The mixture contained two milliliters of Prowl® $H_2O$ mixed in 48 milliliters of water. Forty-five milliliters of the mixture was added to 15,500 milliliters of water. In order to water each flat, 1550 milliliters of the final Prowl® $H_2O$ mixture was added to each flat using a watering can to distribute the water uniformly. After watering, the flats were kept in a closed building for temperature control and then as plants began emerging, the flats were moved to a greenhouse.

Emergence counts were made on Nov. 12, 2009 and again on Nov. 17, 2009. Average plant heights were taken on Nov. 17, 2009. On Nov. 18, 2009, soil was washed away from approximately the top half inch of each flat exposing seeds that were damaged by the Prowl® $H_2O$. The damaged seeds were counted and recorded.

Table 1 shows the results of the field trials established on Nov. 2, 2009. Column one shows the name of the inbred or hybrid that was tested. Column two shows the number of seeds planted of each inbred or hybrid. Column three shows the planting date. Column four shows the total number of plants emerging on Nov. 12, 2009. Column five shows the total number of plants emerging on Nov. 17, 2009. Column six shows the total number of seeds damaged by the Prowl® $H_2O$ herbicide. Column seven shows the total number of seeds that did not germinate. Column eight shows the plant height in inches as of Nov. 17, 2009.

TABLE 1

| Pedigree comparison | Number of Seeds Planted | Planting Date | Total number of Plants Emerged as of Nov. 12, 2009 | Total number of Plants Emerged as of Nov. 17, 2009 | Number of Seeds Damaged by PROWL® $H_2O$ | Number of Seeds Not Germinated | Plant Height (in) on Nov. 17, 2009 |
|---|---|---|---|---|---|---|---|
| SP6493 | 100 | Nov. 2, 2009 | 46 | 56 | 9 | 35 | 2.03 |
| R207 | 100 | Nov. 2, 2009 | 13 | 29 | 60 | 11 | 1.21 |
| SP6493 | 100 | Nov. 2, 2009 | 50 | 58 | 5 | 37 | 1.92 |
| R159 | 100 | Nov. 2, 2009 | 10 | 20 | 62 | 18 | 0.95 |
| SP6493 | 100 | Nov. 2, 2009 | 52 | 61 | 6 | 33 | 2.12 |
| T13 | 100 | Nov. 2, 2009 | 16 | 25 | 50 | 25 | 1.38 |
| SP6493 | 100 | Nov. 2, 2009 | 49 | 60 | 4 | 36 | 1.91 |
| Early Sumac | 100 | Nov. 2, 2009 | 1 | 3 | 77 | 20 | 0.87 |

TABLE 1-continued

| Pedigree comparison | Number of Seeds Planted | Planting Date | Total number of Plants Emerged as of Nov. 12, 2009 | Total number of Plants Emerged as of Nov. 17, 2009 | Number of Seeds Damaged by PROWL ® H₂O | Number of Seeds Not Germinated | Plant Height (in) on Nov. 17, 2009 |
|---|---|---|---|---|---|---|---|
| SP6493 | 100 | Nov. 2, 2009 | 53 | 62 | 7 | 31 | 2.09 |
| R267 | 100 | Nov. 2, 2009 | 13 | 26 | 52 | 22 | 1.80 |
| SP6493 | 100 | Nov. 2, 2009 | 60 | 69 | 7 | 24 | 2.14 |
| R422 | 100 | Nov. 2, 2009 | 9 | 14 | 68 | 18 | 1.41 |
| (A752 × SP6493) Resistant Hybrid | 100 | Nov. 2, 2009 | 41 | 53 | 21 | 26 | 1.63 |
| (A752 × R427) Susceptible Hybrid | 100 | Nov. 2, 2009 | 32 | 38 | 44 | 18 | 1.06 |

As shown in Table 1, inbred line SP6493 showed a significantly higher germination rate when exposed to the herbicide, Prowl® H₂O than the susceptible inbred sorghum lines. Inbred line SP6493 has a germination rate ranging from 46% to 60% as of Nov. 12, 2009 and 53% to 69% on Nov. 17, 2009. In comparison, the susceptible inbred sorghum lines had a germination rate between 1% and 16% as of Nov. 12, 2009 and a germination rage between 3% and 26% as of Nov. 17, 2009. The number of inbred line SP6493 seeds damaged by the Prowl® H₂O herbicide was also significantly less than the seeds of the susceptible inbred lines with SP6493 having between four and nine seed per 100 damaged by the Prowl® H₂O, while in contrast the susceptible inbred lines had between 52 and 77 seed per 100 damaged by the Prowl® H₂O. The herbicide resistant hybrid line also had increased germination rate when exposed to the Prowl® H₂O herbicide with 41 seeds germinated on Nov. 12, 2009 and 53 germinated on Nov. 17, 2009. Only 21 seeds from the herbicide resistant hybrid (A752×SP6493) were damaged while 44 seeds of the herbicide susceptible hybrid (A752×R427) were damaged. Additionally, the plant height recorded on Nov. 17, 2009 demonstrated the increased vigor of the herbicide resistant inbred line SP6493 when compared to the susceptible inbred sorghum lines. The herbicide resistant sorghum hybrid (A752×SP6493) also showed increased vigor when compared to the herbicide susceptible hybrid (A752×R427).

Example 15

2009 Field Trials

On Mar. 26, 2009, in Victoria, Tex., a test of the Dinitroanaline resistance of the present invention was established. 525 pounds of 28-O-0-7 of fertilizer was applied to the land, where seven (7) is micronutrients. Lorsban 15G insecticide was applied at 7.5 pounds per acre. The herbicide Treflan® was applied on Mar. 5, 2009 at three pints per acres with 18 gallons of water per acre. The herbicide was incorporated into the soil by tandem discing, twice, with the discs set at a 45° angle.

The test was established using a four row research cone planter, where a single plot was 12 feet long with 38 inch row spacing. Hybrids (A821×SP6493-1), (A821×SP6493-2), (A752×SP6493-1) and (A752×SP6493-2) containing the SP6493 mutation with dinitroanaline herbicide resistance were compared to one hybrid line NK7829 that was susceptible to dinitroanaline herbicides. One hundred seeds were planted per plot. The data was recorded on May 15, 2009 and included emergence data only, including the number of plants that emerged.

Table 2 shows the number of plants emerging on May 15, 2009. Column one shows the cultivar name, column two shows the first replication. Column three shows the results of the second replication. Column four shows the average of the two replications.

TABLE 2

| Hybrid Sorghum Cultivar | Replication 1 | Replication 2 | Two Replication Average |
|---|---|---|---|
| (A821 × SP6493-1) | 15 | 12 | 8.50 |
| (A752 × SP6493-1) | 40 | 20 | 30.00 |
| NK7829 | 8 | 1 | 4.50 |
| (A821 × SP6493-2) | 18 | 18 | 18.00 |
| (A752 × SP6493-2) | 14 | 16 | 15.00 |
| NK7829 | 5 | 2 | 3.50 |

As shown in Table 2, the hybrid sorghum lines with resistance to the dinitroanaline herbicide had a significantly higher number of plants emerging with an average number of emerging plants between 8.5 and 30.00, with the dinitroanaline susceptible hybrid sorghum line NK7829 having an average number of emerging plants between 3.50 and 4.50, a percent increased resistance between 143% and 757%.

Example 16

2009 Field Trials

On Apr. 21, 2009, in Victoria, Tex., a test of the Dinitroanaline resistance of the present invention was established. 525 pounds of 28-O-0-7 of fertilizer was applied to the land, where seven (7) is micronutrients. Lorsban 15G insecticide was applied at 7.5 pounds per acre. The herbicide Treflan® was applied on Mar. 5, 2009 at two pints per acres with 18 gallons of water per acre. The herbicide was incorporated into the soil by tandem discing, twice, with the discs set at a 45° angle.

The test was established using a four row research cone planter, where a single plot was 12 feet long with 38 inch row spacing. Hybrids (A821×SP6493-1), (A821×SP6493-2), (A752×SP6493-1) and (A752×SP6493-2) containing the SP6493 mutation with dinitroanaline herbicide resistance were compared to one hybrid line NK7829 that was susceptible to dinitroanaline herbicides. One hundred seeds were planted per plot. The data was recorded on May 15, 2009 and included emergence data only, including the number of plants that emerged.

Table 3 shows the number of plants emerging on May 15, 2009. Column one shows the cultivar name, column two shows the first replication. Column three shows the results of the second replication. Column four shows the results of the third replication. Column five shows the results of the fourth replication and column six shows average of the four replications.

TABLE 3

| Hybrid Sorghum | Replication 1 | Replication 2 | Replication 3 | Replication 4 | Four Replication Average |
|---|---|---|---|---|---|
| NK7829 | 44 | 23 | 2 | 7 | 19.00 |
| (A821 × SP6493-1) | 75 | 62 | 12 | 15 | 41.00 |
| (A752 × SP6493-1) | 63 | 61 | 20 | 40 | 46.00 |
| NK7829 | 30 | 29 | 1 | 8 | 17.00 |
| (A821 × SP6493-2) | 71 | 39 | 18 | 18 | 36.50 |
| (A752 × SP6493-2) | 64 | 89 | 16 | 14 | 45.75 |
| NK7829 | 43 | 23 | 2 | 5 | 18.25 |

As shown in Table 3, the hybrid sorghum lines containing the SP6493 mutation with resistance to the dinitroanaline herbicide had a significantly higher number of plants emerging. The Hybrid sorghum lines with resistance to dinitroanalines herbicides had an average number of emerging plants between 36.50 and 46.00, with the dinitroanaline susceptible hybrid sorghum line NK7829 having an average number of emerging plants between 17.00 and 19.00, a percent increased resistance of between 115% and 170%.

Example 17

2009 Field Trials

Table 4 shows a comparison of eleven resistant sorghum hybrids containing the SP6493 mutation versus susceptible hybrid sorghum lines. The trial was planted on Aug. 12, 2009 with 50 seeds planted of eleven resistant hybrid lines and four susceptible hybrid sorghum lines. The resistant hybrids sorghum lines were (A752×SP6493), (A781×SP6493), (A787×SP6493), (A810×SP6493), (A830×SP6493), (A938×SP6493), (A940×SP6493), (A947×SP6493), (A961×SP6493), (A962×SP6493), and (A964×SP6493). The susceptible hybrids sorghum lines were NK7829, NK6673, K73-J6, and 1486. Six replications of the each entry were planted in a Randomized Complete Block Experimental Design. Prowl® H$_2$O was sprayed immediately after planting at a rate of two quarts per acre. Irrigation was then applied to aid in seed germination and Prowl® H$_2$O incorporation. In Table 4 column one shows the testing year, column two shows the testing location, column three shows the hybrid sorghum cultivar type, column four shows the number of emerging plants and column five shows the percent of emergence. Row five shows the Grand Mean. Row six shows the CV. Row seven shows the LSD. Row eight shows the number of replications that were made.

TABLE 4

| Year | Location | Hybrid | Number of Emergent plants | Percent Emergence (%) |
|---|---|---|---|---|
| 2009 | Victoria, Texas | Resistant | 28.3 | 56.6 |
| 2009 | Victoria, Texas | Susceptible | 18.8 | 37.6 |
| | | Grand Mean | | 51.6 |
| | | CV | | 27.4 |
| | | LSD | | 2.5 |
| | | Replications | | 6 |

As shown in Table 4, the hybrid sorghum lines containing the SP6493 mutation with resistance to the dinitroanaline herbicide had a significantly higher number of plants emerging. The resistant hybrid sorghum lines had an average percentage of emerging plants of 56.6% while the dinitroanaline susceptible hybrid sorghum lines had an average percentage of emerging plants of 37.6%, a difference of 19.0% or a percent increased increase resistance of 50.5%, which was significant based upon the LSD of 2.5.

Example 18

2009 Field Trials

Table 5 shows a breakout of the individual resistant sorghum hybrids containing the SP6493 mutation versus the individual susceptible hybrid sorghum lines as shown in Table 4. The trial was planted on Aug. 12, 2009 with 50 seeds planted, including eleven resistant hybrid lines and four susceptible hybrid sorghum lines. The resistant hybrids were (A752×SP6493), (A781×SP6493), (A787×SP6493), (A810×SP6493), (A830×SP6493), (A938×SP6493), (A940×SP6493), (A947×SP6493), (A961×SP6493), (A962×SP6493), and (A964×SP6493). The susceptible hybrids were NK7829, NK6673, K73-J6, and 1486. Six replications of the each entry were planted in a Randomized Complete Block Experimental Design. Prowl® H$_2$O was sprayed immediately after planting at a rate of two quarts per acre. Irrigation was then applied to aid in seed germination and Prowl® H$_2$O incorporation. In Table 5 column one shows the testing year, column two shows the testing location, column three shows the hybrid cultivar name, column four shows the number of emerging plants and column five shows the percent of emergence. Row five shows the Grand Mean. Row six shows the CV. Row seven shows the LSD. Row eight shows the number of replications that were made.

TABLE 5

| Year | Location | Hybrid | Number of Emergent plants | Percent Emergence (%) |
|---|---|---|---|---|
| 2009 | Victoria, Texas | (A938 × SP6493) | 33.7 | 67.4 |
| 2009 | Victoria, Texas | (A964 × SP6493) | 32.0 | 64.0 |
| 2009 | Victoria, Texas | (A830 × SP6493) | 31.8 | 63.6 |
| 2009 | Victoria, Texas | (A940 × SP6493) | 29.2 | 58.4 |
| 2009 | Victoria, Texas | (A961 × SP6493) | 28.7 | 57.4 |
| 2009 | Victoria, Texas | (A810 × SP6493) | 27.3 | 54.6 |
| 2009 | Victoria, Texas | (A962 × SP6493) | 27.2 | 54.4 |
| 2009 | Victoria, Texas | (A787 × SP6493) | 25.7 | 51.4 |
| 2009 | Victoria, Texas | (A781 × SP6493) | 25.5 | 51.0 |
| 2009 | Victoria, Texas | (A947 × SP6493) | 25.5 | 51.0 |
| 2009 | Victoria, Texas | (A752 × SP6493) | 25.2 | 50.4 |
| 2009 | Victoria, Texas | K73-J6 | 21.7 | 43.4 |
| 2009 | Victoria, Texas | NK7633 | 19.3 | 38.6 |
| 2009 | Victoria, Texas | NK7829 | 17.7 | 35.4 |
| 2009 | Victoria, Texas | 1486 | 16.0 | 32.0 |
| | | Grand Mean | | 51.6 |
| | | CV | | 27.4 |
| | | LSD | | 6.8 |
| | | Replications | | 6 |

As shown in Table 5, each individual resistant sorghum hybrid had a significantly higher percent emergence than each of the susceptible hybrids. The individual hybrid sorghum lines with resistance to dinitroanaline herbicides had an average number of emerging plants of 56.6% while the dinitroanaline herbicide susceptible hybrid sorghum lines had an average number of emerging plants of 37.6%, a difference of 19.0% or a percent increased increase resistance of 50.5%, which was significant based upon the LSD of 6.8.

Example 19

2009 Field Trials

Table 6 shows a comparison of the resistant sorghum inbred SP6493 containing the SP6493 mutation versus susceptible inbred sorghum lines R159, R207, A752, and A821. The trial was planted on Aug. 12, 2009 with 100 seeds planted of each line. Eight replications of the each entry were planted in a Randomized Complete Block Experimental Design. Prowl® H$_2$O was sprayed immediately after planting at a rate of two quarts per acre. Irrigation was then applied to aid in seed germination and Prowl® H$_2$O incorporation. Column one shows the testing year, column two shows the testing location, column three shows the inbred cultivar name, column four shows the number of emerging plants and column five shows the percent of emergence. Row five shows the Grand Mean. Row six shows the CV. Row seven shows the LSD. Row eight shows the number of replications that were made.

TABLE 6

| Year | Location | Inbred | Number of Emergent plants | Percent Emergence (%) |
|---|---|---|---|---|
| 2009 | Victoria, Texas | SP6493 | 43.9 | 43.9 |
| 2009 | Victoria, Texas | Susceptible inbred lines | 26.1 | 26.1 |
| | | Grand Mean | | 29.7 |
| | | CV | | 50.6 |
| | | LSD | | 8.0 |
| | | Replications | | 8 |

As shown in Table 6, the sorghum inbred cultivar SP6493 has a significantly higher percentage of emerging plants with a 43.9% emergence compared to the susceptible inbred sorghum lines with the 26.1% emergence, a difference of 17.8% or a percent increased resistance of 68%, which was significant based upon the LSD of 8.0.

Example 20

2009 Field Trials

Table 7 shows a comparison of the resistant sorghum inbred line SP6493 containing the SP6493 mutation versus the susceptible inbred sorghum lines R159, R207, A752, and A821. The trial was planted on Aug. 12, 2009 with 100 seeds planted of each inbred were planted using the inbred sorghum lines SP6493, A752, A821, R207 and R159. Eight replications of the each entry were planted in a Randomized Complete Block Experimental Design. Prowl® H$_2$O was sprayed immediately after planting at a rate of two quarts per acre. Irrigation was then applied to aid in seed germination and Prowl® H$_2$O incorporation. Column one shows the testing year, column two shows the testing location, column three shows the inbred sorghum line name, column four shows the number of emerging plants and column five shows the percent of emergence. Row eight shows the Grand Mean. Row nine shows the CV. Row ten shows the LSD. Row eleven shows the number of replications that were made.

TABLE 7

| Year | Location | Inbred | Number of Emergent plants | Percent Emergence (%) |
|---|---|---|---|---|
| 2009 | Victoria, Texas | SP6493 | 43.9 | 43.9 |
| 2009 | Victoria, Texas | A752 | 38.8 | 38.8 |
| 2009 | Victoria, Texas | A821 | 25.5 | 25.5 |
| 2009 | Victoria, Texas | R207 | 21.6 | 21.6 |
| 2009 | Victoria, Texas | R159 | 18.5 | 18.5 |
| | | Grand Mean | | 29.7 |
| | | CV | | 45.3 |
| | | LSD | | 11.4 |
| | | Replications | | 8 |

As shown in Table 7, the sorghum inbred cultivar SP6493 has a significantly higher percentage of emerging plants with a 43.9% emergence compared to the susceptible sorghum inbred line R207 with an emergence of 21.6%, a percent increased resistance of 104.6%. SP6493 was also significantly higher than sorghum inbred line R159 which had an emergence of 18.5%, a percent increased resistance of 137.3%. SP6493 also was significantly higher than the sorghum inbred line A821, which had an emergence of 25.5%, a percent increased resistance of 71.8%. SP6493 was also higher than the sorghum inbred line A752 that had an emergence of 38.8%. This increased resistance was 13.1%.

FURTHER EMBODIMENTS OF THE INVENTION

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed and the present invention, in particular embodiments, also relates to transformed versions of the claimed variety or line.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed sorghum plants using transformation methods as described below to incorporate transgenes into the genetic material of the sorghum plant(s).

Plant Transgenics

Heterologous genes intended for expression in plants are first assembled in expression vectors containing a heterologous gene and appropriate transcriptional and translational control elements, methods of which are well known to those skilled in the art. Methods include in vitro recombinant DNA techniques, synthetic techniques, and in vivo genetic recombination. Exemplary techniques are widely described in the art (See e.g., Sambrook. et al. (1989) Molecular Cloning, A Laboratory Manual, Cold Spring Harbor Press, Plainview, N.Y., and Ausubel, F. M. et al (1989) Current Protocols in Molecular Biology, John Wiley & Sons, New York, N.Y., herein incorporated by reference).

In general, these vectors comprise a nucleic acid sequence encoding a heterologous gene operably linked to a promoter and other regulatory sequences (e.g., enhancers, polyadenylation signals, etc.) required for expression in a plant.

Promoters include, but are not limited to, constitutive promoters, tissue-, organ-, and developmentally-specific promoters, and inducible promoters. Examples of promoters include, but are not limited to; constitutive promoter 35S of cauliflower mosaic virus; a wound-inducible promoter from tomato, leucine amino peptidase (Chao et al., 1999, Plant Physiol 120:979-992, herein incorporated by reference in its entirety); a chemically-inducible promoter from tobacco, Pathogenesis-Related 1 (induced by salicylic acid and benzothiadiazole-7-carbothioic acid S-methyl ester); a heat shock promoter (U.S. Pat. No. 5,187,267, herein incorporated by reference in its entirety); a tetracycline-inducible promoter (U.S. Pat. No. 5,057,422, herein incorporated by reference in its entirety); and seed-specific promoters.

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters such as those disclosed herein. Transcriptional terminators are responsible for the termination of transcription beyond the transcript and its correct polyadenylation. Appropriate transcriptional terminators and those which are known to function in plants include, but are not limited to, the CaMV 35S terminator, the tm1 terminator, the pea rbcS E9 terminator, and the nopaline and octopine synthase terminator (Odell et al., 1985, Nature 313:810; Rosenberg et al., 1987, Gene, 56:125; Guerineau et al., 1991, Mol. Gen. Genet. 262:141; Proudfoot, 1991, Cell, 64:671; Sanfacon et al., 1990, Genes Dev. 5:141; Mogen et al., 1990, Plant Cell, 2:1261; Munroe et al., 1990, Gene, 91:151; Ballas et al., 1989, Nucleic Acids Res. 17:7891; Joshi et al., 1987, Nucleic Acid Res., 15:9627, all of which are incorporated herein by reference in their entireties).

In some embodiments, constructs for expression of the heterologous gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. Intron sequences have been routinely incorporated into plant transformation vectors, typically within the non-translated leader.

In some embodiments, a construct for expression of the heterologous nucleic acid sequence of interest also includes a regulator such as a nuclear localization signal (Kalderon et al., 1984, Cell 39:499; Lassner et al., 1991, Plant Molecular Biology 17:229), a plant translational consensus sequence (Joshi, 1987, Nucleic Acids Research 15:6643), an intron (Luehrsen and Walbot, 1991, Mol. Gen. Genet. 225:81), and the like, operably linked to the nucleic acid sequence encoding an heterologous gene.

In preparing the construct comprising the nucleic acid sequence encoding a heterologous gene, or encoding a sequence designed to decrease heterologous gene expression, various DNA fragments can be manipulated so as to provide for the DNA sequences in the desired orientation (e.g., sense or antisense) and, as appropriate, in the desired reading frame. For example, adapters or linkers can be employed to join the DNA fragments, or other manipulations can be used to provide for convenient restriction sites, removal of superfluous DNA, removal of restriction sites, and the like. For this purpose, in vitro mutagenesis, primer repair, restriction, annealing, resection, ligation, and the like is preferably employed, where insertions, deletions or substitutions (e.g., transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra, 1982, Gene 19: 259; Bevan et al., 1983, Nature 304:184, all of which are incorporated herein by reference), the bar gene which confers resistance to the herbicide phosphinothricin (White et al., 1990. Nucl Acids Res. 18:1062; Spencer et al., 1990. Theor. Appl. Genet. 79:625, all of which are incorporated herein by reference in their entireties), the hph gene which confers resistance to the antibiotic hygromycin (Blochlinger and Diggelmann, 1984, Mol. Cell. Biol. 4:2929, incorporated herein by reference in its entirety), and the dhfr gene that confers resistance to methotrexate (Bourouis et al., 1983, EMBO J., 2:1099, incorporated herein by reference in its entirety).

In some embodiments, the Ti (T-DNA) plasmid vector is adapted for use in an *Agrobacterium* mediated transfection process such as in U.S. Pat. No. 6,369,298 (sorghum), and U.S. Pat. Nos. 5,981,839, 6,051,757, 5,981,840, 5,824,877 and 4,940,838 all of which are incorporated by reference herein in their entireties. Construction of recombinant Ti and Ri plasmids in general follows methods typically used with more common vectors, such as pBR322. Additional use can be made of accessory genetic elements sometimes found with the native plasmids and sometimes constructed from foreign sequences. These may include, but are not limited to, structural genes for antibiotic resistance as selection genes.

There are two systems of recombinant Ti and Ri plasmid vector systems now in use. The first system is called the "co-integrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The use of T-DNA as a flanking region in a construct for integration into a Ti- or R1-plasmid has been described in EPO No. 116,718 and PCT Application Nos. WO 84/02913, 02919 and 02920; Herrera-Estrella, 1983, Nature 303:209-213; Fraley et al., 1983, Proc. Natl. Acad. Sci, USA 80:4803-4807; Horsch et al., 1984, Science 223:496-498; and DeBlock et al., 1984, EMBO J. 3:1681-1689, all of which are herein incorporated by reference in their entireties.

The second system is called the "binary" system in which two plasmids are used and the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

In some embodiments, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (U.S. Pat. No. 5,501,967 herein incorporated by reference in its entirety). One of skill in the art knows that homologous recombination may be achieved using targeting vectors that contain sequences that are homologous to any part of the targeted plant gene, whether belonging to the regulatory elements of the gene or the coding regions of the gene. Homologous recombination may be achieved at any region of a plant gene so long as the nucleic acid sequence of regions flanking the site to be targeted is known. *Agrobacterium tumefaciens* is a common soil bacterium that causes crown gall disease by transferring some of its DNA to the plant host. The transferred DNA (T-DNA) is stably integrated into the plant genome, where its expression leads to the synthesis of plant hormones and thus to the tumorous growth of the cells. A putative macromolecular complex forms in the process of T-DNA transfer out of the bacterial cell into the plant cell.

In some embodiments, the nucleic acids as disclosed herein are utilized to construct vectors derived from plant (+) RNA viruses (e.g., brome mosaic virus, tobacco mosaic virus, alfalfa mosaic virus, cucumber mosaic virus, tomato mosaic virus, and combinations and hybrids thereof). Generally, the inserted heterologous polynucleotide can be expressed from these vectors as a fusion protein (e.g., coat protein fusion protein) or from its own subgenomic promoter or another promoter. Methods for the construction and use of such viruses are described in U.S. Pat. Nos. 5,846,795; 5,500,360; 5,173,410; 5,965,794; 5,977,438; and 5,866,785, all of which are incorporated herein by reference in their entireties.

Once a nucleic acid sequence encoding the heterologous gene is operatively linked to an appropriate promoter and inserted into a suitable vector for the particular transformation technique utilized (e.g., one of the vectors described above), the recombinant DNA described above can be introduced into the plant cell in a number of art-recognized ways. Those skilled in the art will appreciate that the choice of method depends on the type of plant targeted for transformation. In some embodiments, the vector is maintained episomally. In some embodiments, the vector is integrated into the genome. In some embodiments, direct transformation in the plastid genome is used to introduce the vector into the plant cell (for example, see U.S. Pat. Nos. 5,451,513; 5,545,817; 5,545,818; PCT application WO 95/16783 all of which are incorporated herein by reference in their entireties).

The basic technique for chloroplast transformation involves introducing regions of cloned plastid DNA flanking a selectable marker together with the nucleic acid encoding the sequences of interest into a suitable target tissue (e.g., using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al., 1990, Proc. Natl. Acad. Sci., 87:8526; Staub and Maliga, 1992, Plant Cell, 4:39, all of which are incorporated herein by reference). The presence of cloning sites between these markers allows creation of a plastid targeting vector introduction of foreign DNA molecules (Staub and Maliga, 1993, EMBO J., 12:601). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga, 1993, Proc. Natl. Acad. Sci., 90:913). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of RNAs encoded by the DNA molecule.

In one embodiment, vectors useful in the practice of the present invention are microinjected directly into plant cells (Crossway, 1985, Mol. Gen. Genet, 202:179). In some embodiments, the vector is transferred into the plant cell by using polyethylene glycol (Krens et al., 1982, Nature, 296:72; Crossway et al., 1986, BioTechniques, 4:320); fusion of protoplasts with other entities such as minicells, cells, lysosomes or other fusible lipid-surfaced bodies (Fraley et al., 1982, Proc. Natl. Acad. Sci., USA, 79:1859); and protoplast transformation (EP 0 292 435); direct gene transfer (Paszkowski et al., 1984, EMBO J., 3:2717; Hayashimoto et al., 1990, Plant Physiol. 93:857).

In some embodiments, the vector may also be introduced into the plant cells by electroporation. (Fromm, et al., 1985, Proc. Natl. Acad. Sci. USA 82:5824; Riggs et al., 1986, Proc. Natl. Acad. Sci. USA 83:5602). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus. In addition to direct transformation, in some embodiments, the vectors comprising a nucleic acid sequence encoding a heterologous gene are transferred using *Agrobacterium*-mediated transformation (Hinchee et al., 1988, Biotechnology, 6:915; Ishida et al., 1996, Nature Biotechnology 14:745, all of which are herein incorporated by reference). *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (e.g., nucleic acid sequences operatively linked to a promoter of the present invention) can be introduced into appropriate plant cells, by means of the Ti plasmid of *Agrobacterium tumefaciens* (previously described). The Ti plasmid is transmitted to plant cells on infection by *Agrobacterium tumefaciens*, and is stably integrated into the plant genome (Schell, 1987, Science, 237: 1176). Species that are susceptible to infection by *Agrobacterium* may be transformed in vitro. Transformation methods for producing transgenic sorghum plants using *Agrobacterium*-mediated transformation are provided in U.S. Pat. No. 6,369,298.

In some embodiments, the vector is introduced through ballistic particle acceleration (U.S. Pat. No. 4,945,050; Casas et al., 1993, Proc. Natl. Acad. Sci. USA 90:11212, all references are incorporated herein in their entireties).

In some embodiments, after selecting for transformed plant material that can express a heterologous gene encoding a heterologous protein or variant thereof, whole plants are regenerated. Plant regeneration from cultured protoplasts is described in Evans et al., Handbook of Plant Cell Cultures, Vol. 1: (MacMillan Publishing Co. New York, (1983); Vasil I. R. (ed.), Cell Culture and Somatic Cell Genetics of Plants, Acad. Press, Orlando, Vol. I, (1984) and Vol. III, (1986), incorporated herein by reference in their entireties. It is known that many plants can be regenerated from cultured cells or tissues including, but not limited to, all major species of sugarcane, sugar beet, cotton, fruit and other trees, legumes and vegetables, and monocots (e.g., the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins Shoots and roots normally develop simultaneously. Efficient regeneration will depend on the medium, on the genotype, and on the history of the culture. The reproducibility of regeneration depends on the control of these variables.

Expression Vectors for Sorghum Transformation: Marker Genes

Expression vectors include at least one genetic marker operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., *Proc. Natl. Acad. Sci. USA,* 80:4803 (1983). Another commonly used selectable marker gene is the hygromycin phosphotransferase gene which confers resistance to the antibiotic hygromycin. Vanden Elzen et al., *Plant Mol. Biol.,* 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford et al., *Plant Physiol.* 86:1216 (1988), Jones et al., *Mol. Gen. Genet.,* 210:86 (1987), Svab et al., *Plant Mol. Biol.* 14:197 (1990), Hille et al., *Plant Mol. Biol.* 7:171 (1986)). Other selectable marker genes confer resistance to herbicides such as glyphosate, glufosinate or bromoxynil (Comai et al., *Nature* 317:741-744 (1985), Gordon-Kamm et al., *Plant Cell* 2:603-618 (1990) and Stalker et al., *Science* 242:419-423 (1988)).

Selectable marker genes for plant transformation not of bacterial origin include, for example, mouse dihydrofolate reductase, plant 5-enolpyruvylshikimate-3-phosphate synthase and plant acetolactate synthase (Eichholtz et al., *Somatic Cell Mol. Genet.* 13:67 (1987), Shah et al., *Science* 233:478 (1986), Charest et al., *Plant Cell Rep.* 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase (Jefferson, R. A., *Plant Mol. Biol. Rep.* 5:387 (1987), Teeri et al., *EMBO J.* 8:343 (1989), Koncz et al., *Proc. Natl. Acad. Sci. USA* 84:131 (1987), DeBlock et al., *EMBO J.* 3:1681 (1984)).

In vivo methods for visualizing GUS activity that do not require destruction of plant tissue are available (Molecular Probes publication 2908, IMAGENE GREEN, p. 1-4 (1993) and Naleway et al., *J. Cell Biol.* 115:151a (1991)). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells (Chalfie et al., *Science* 263: 802 (1994)). GFP and mutants of GFP may be used as screenable markers.

Expression Vectors for Sorghum Transformation: Promoters

Genes included in expression vectors must be driven by a nucleotide sequence comprising a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters that initiate transcription only in a certain tissue are referred to as "tissue-specific". A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

Inducible Promoters—An inducible promoter is operably linked to a gene for expression in Sorghum. Optionally, the inducible promoter is operably linked to a nucleotide sequence encoding a signal sequence which is operably linked to a gene for expression in Sorghum. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Mett et al., *Proc. Natl. Acad. Sci. USA* 90:4567-4571 (1993)); In2 gene from maize which responds to benzenesulfonamide herbicide safeners (Hershey et al., *Mol. Gen. Genetics* 227:229-237 (1991) and Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. USA* 88:0421 (1991)).

Constitutive Promoters—A constitutive promoter is operably linked to a gene for expression in sorghum or the constitutive promoter is operably linked to a nucleotide sequence encoding a signal sequence which is operably linked to a gene for expression in sorghum.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2: 163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)). The ALS promoter, Xba1/Nco1 fragment 5' to the *Brassica napus* ALS3 structural gene (or a nucleotide sequence similarity to said Xba1/Nco1 fragment), represents a particularly useful constitutive promoter. See PCT application WO 96/30530.

Tissue-specific or Tissue-preferred Promoters—A tissue-specific promoter is operably linked to a gene for expression in sorghum. Optionally, the tissue-specific promoter is operably linked to a nucleotide sequence encoding a signal sequence which is operably linked to a gene for expression in sorghum. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai et al., *Science* 23:476-482 (1983) and Sengupta-Gopalan et al., *Proc. Natl. Acad. Sci. USA* 82:3320-3324 (1985)); a leaf-specific and light-induced promoter such as that from cab or rubisco (Simpson et al., *EMBO J.* 4(11): 2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., *Plant Mol. Biol.* 20:49 (1992); Close, P. S., Master's Thesis, Iowa State University (1993); Knox, C., et al., *Plant Mol. Biol.* 9:3-17 (1987); Lerner et al., *Plant Physiol.* 91:124-129 (1989); Frontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is a sorghum plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*, CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example Jones et al., *Science* 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al. *Cell* 78:1089 (1994) (*Arabidopsis* RSP2 gene for resistance to *Pseudomonas syringae*).

B. A gene conferring resistance to a pest, such as soybean cyst nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US 93/06487 which teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., which discloses genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene.

L. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

M. A hydrophobic moment peptide. See PCT application WO 95/16776, which discloses peptide derivatives of tachyplesin which inhibit fungal plant pathogens, and PCT application WO 95/18855 which teaches synthetic antimicrobial peptides that confer disease resistance.

N. A membrane permease, a channel former or a channel blocker. For example, see the disclosure of Jaynes et al., *Plant Sci* 89:43 (1993), of heterologous expression of a cecropin-β lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus and tobacco mosaic virus.

P. An insect-specific antibody or an immunotoxin derived therefrom. Thus, an antibody targeted to a critical metabolic function in the insect gut would inactivate an affected enzyme, killing the insect. See Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., *Nature* 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

S. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S., *Current Biology*, 5(2) (1995).

U. Antifungal genes. See Cornelissen and Melchers, *Plant Physiol.*, 101:709-712 (1993); Parijs et al., *Planta* 183:258-264 (1991) and Bushnell et al., *Can. J. of Plant Path.* 20(2): 137-149 (1998).

V. Genes that confer resistance to *Phytophthora* root rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., *Phytophthora* Root Rot Resistance Gene Mapping in Soybean, Plant Genome IV Conference, San Diego, Calif. (1995).

2. Genes That Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *Bio/Technology* 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall et al., *Theor. Appl. Genet.* 83:435 (1992).

C. An herbicide that inhibits photosynthesis, such as a triazine (psbA and gs+ genes) and a benzonitrile (nitrilase gene). Przibila et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441 and 67442. Cloning and expression of DNA coding for a glutathione S-transferase is described by Hayes et al., *Biochem. J.* 285:173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., *Plant Physiol.*, 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes That Confer or Contribute to a Value-Added Trait, such as:

A. Modified fatty acid metabolism, for example, by transforming a plant with an antisense gene of stearyl-ACP desaturase to increase stearic acid content of the plant. See Knultzon et al., *Proc. Natl. Acad. Sci. USA* 89:2625 (1992).

B. Decreased phytate content—1) Introduction of a phytase-encoding gene enhances breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. This could be accomplished by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteriol.* 170:810 (1988) (nucleotide sequence of *Streptococcus mutants* fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus licheniformis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

D. Elevated oleic acid via FAD-2 gene modification and/or decreased linolenic acid via FAD-3 gene modification. See U.S. Pat. Nos. 6,063,947; 6,323,392; and international publication WO 93/11245.

4. Genes that Control Male Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., *Plant Mol. Biol.* 19:611-622, 1992).

Methods for Sorghum Transformation

Numerous methods for plant transformation have been developed including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc. Boca Raton, 1993) pages 67-88. In addition, expression vectors and in-vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A. *Agrobacterium*-mediated Transformation

One method for introducing an expression vector into plants is based on the natural transformation system of *Agrobacterium*. See, for example, Horsch et al., Science 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*

10:1 (1991). Descriptions of *Agrobacterium* vector systems and methods for *Agrobacterium*-mediated gene transfer are provided by Gruber et al., supra, Miki et al., supra and Moloney et al., *Plant Cell Reports* 8:238 (1989). See also, U.S. Pat. No. 5,563,055 (Townsend and Thomas), issued Oct. 8, 1996.

B. Direct Gene Transfer

Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987); Sanford, J. C., *Trends Biotech.* 6:299 (1988); Klein et al., *Bio/Tech.* 6:559-563 (1988); Sanford, J. C. *Physiol Plant* 7:206 (1990); Klein et al., *Biotechnology* 10:268 (1992). See also U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.,* 4:2731 (1985); Christou et al., *Proc Natl. Acad. Sci. USA* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described (Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994)).

Following transformation of sorghum target tissues, expression of the above-described selectable marker genes allows for preferential selection of transformed cells, tissues and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular sorghum line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple X by Y cross or the process of backcrossing depending on the context.

Single-Gene Conversions

When the term "Sorghum plant" is used in the context of the present invention, this also includes any single gene conversions of that variety. The term single gene converted plant as used herein refers to those sorghum plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental sorghum plant that contributes the gene for the desired characteristic is termed the nonrecurrent or donor parent. This terminology refers to the fact that the nonrecurrent parent is used one time in the backcross protocol and therefore does not recur. The parental sorghum plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a sorghum plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross; one of the major purposes is to add some agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic; examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185; 5,973,234 and 5,977,445; the disclosures of which are specifically hereby incorporated by reference.

Tissue Culture

Further reproduction of a variety can occur by tissue culture and regeneration. Tissue culture of various tissues of sorghum and regeneration of plants therefrom is well known and widely published. For example, reference may be had to Jelaska, S. et al., *Physiol. Plant.* 64(2):237-242 (1985) and Krsnik-Rasol, M., *Int. J. Dev. Biol.* 35(3):259-263 (1991).

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, pistils and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

DEPOSIT INFORMATION

A deposit of the Sorghum Partners, Inc. proprietary sorghum seed containing the allele designated SP6493 has been made with the American Type Culture Collection (ATCC), 10801 University Boulevard, Manassas, Va. 20110. This deposit is made up of two sorghum cultivar lines containing the allele SP6493 with resistance to dinitroanaline herbicides. The date of deposit was Dec. 11, 2008. The deposit of 2,500 seeds was taken from the same deposit maintained by Sorghum Partners, Inc. since prior to the filing date of this application. The deposit is intended to meet all of the requirements of 37 C.F.R. 1.801-1.809. Upon allowance of any claims in this application, all restrictions on the availability to the public of the variety will be irrevocably removed by affording access to a deposit of at least 2,500 seeds of the same variety with the American Type Culture Collection, Manassas, Va. The ATCC accession number is PTA-9658. The deposit will be maintained in the depository for a period of 30 years, or 5 years after the last request, or for the effective life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

I claim:

1. A sorghum seed containing an allele which confers resistance to dinitroanaline herbicides designated SP6493, wherein said seed containing said SP6493 allele has been deposited under ATCC Accession No. PTA-9658.

2. A sorghum plant produced by growing the seed of claim 1.

3. Pollen of the plant of claim 2.

4. An ovule of the plant of claim 2.

5. A tissue culture comprising regenerable cells of the plant of claim 2.

6. A sorghum plant regenerated from said tissue culture of claim 5.

7. A method for producing F1 hybrid sorghum seed comprising crossing a first parent sorghum plant with a second parent sorghum plant and harvesting the resultant F1 hybrid sorghum seed, wherein first or second parent sorghum seed is the sorghum of claim 2.

8. A first generation (F1) hybrid sorghum plant produced by growing said hybrid sorghum seed of claim 7.

9. A sorghum seed produced by growing the plant of claim 8.

10. Pollen of the plant of claim 8, wherein said pollen confers to a sorghum plant grown from a seed made with the pollen that is resistant or tolerant to one or more dinitroanaline herbicides.

11. An ovule of the plant of claim 8.

12. A tissue culture comprising regenerable cells of the plant of claim 8.

13. A sorghum plant regenerated from said tissue culture of claim 12.

* * * * *